(12) United States Patent
Fredrikson

(10) Patent No.: US 11,850,253 B2
(45) Date of Patent: Dec. 26, 2023

(54) TWO COMPONENT COMPOSITIONS

(71) Applicant: Asamedic AS, Kolbotn (NO)

(72) Inventor: John Bjorn Fredrikson, Elverum (NO)

(73) Assignee: Asamedic AS, Kolbotn (NO)

( * ) Notice: Subject to any disclaimer, the term of this patent is extended or adjusted under 35 U.S.C. 154(b) by 373 days.

(21) Appl. No.: 16/956,137

(22) PCT Filed: Dec. 20, 2018

(86) PCT No.: PCT/EP2018/086260
§ 371 (c)(1),
(2) Date: Jun. 19, 2020

(87) PCT Pub. No.: WO2019/122165
PCT Pub. Date: Jun. 27, 2019

(65) Prior Publication Data
US 2021/0077507 A1  Mar. 18, 2021

(30) Foreign Application Priority Data

Dec. 22, 2017 (EP) .................................. 17210437

(51) Int. Cl.
*A61K 31/616* (2006.01)
*A61K 9/08* (2006.01)
*A61K 47/02* (2006.01)
*C07C 65/10* (2006.01)

(52) U.S. Cl.
CPC .............. *A61K 31/616* (2013.01); *A61K 9/08* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 5,157,030 A | 10/1992 | Galat | |
| 5,776,431 A | 7/1998 | Galat | |
| 7,029,701 B2 | 4/2006 | Chen | |
| 2005/0008690 A1 | 1/2005 | Miller | |
| 2007/0045134 A1 | 3/2007 | Dvorak et al. | |
| 2010/0125242 A1 | 5/2010 | Phykitt | |
| 2012/0316140 A1 | 12/2012 | Phykitt | |
| 2020/0316095 A1 | 10/2020 | Gorbitz | |
| 2021/0212976 A1 | 7/2021 | Fredrikson | |
| 2022/0218724 A1 | 7/2022 | Fredrikson | |

FOREIGN PATENT DOCUMENTS

| | | |
|---|---|---|
| CN | 1418635 A | 5/2003 |
| CN | 101632647 A | 1/2010 |
| EP | 0411590 A2 | 2/1991 |
| EP | 1428525 A1 | 6/2004 |
| EP | 2777802 A1 | 9/2014 |
| GB | 912894 A | 12/1962 |
| GB | 1525765 A | 9/1978 |
| GB | 2321231 A | 7/1998 |
| JP | 11222457 A | 8/1999 |
| JP | 2008507574 A | 3/2008 |
| WO | 9838104 A1 | 9/1998 |
| WO | 199838104 A1 | 9/1998 |
| WO | 0066456 A2 | 11/2000 |
| WO | 200066456 A2 | 11/2000 |
| WO | 200209666 A1 | 2/2002 |
| WO | 2004002177 A1 | 12/2003 |
| WO | 2006104086 A1 | 10/2006 |
| WO | 2009007768 A1 | 1/2009 |
| WO | 2010128977 A1 | 11/2010 |
| WO | 2014048881 A1 | 4/2014 |
| WO | 2015061521 A1 | 4/2015 |
| WO | 2017001468 A1 | 1/2017 |
| WO | 2018002124 A1 | 1/2018 |

OTHER PUBLICATIONS

Aspirin,; from Chemical Stability of Pharmaceuticals, A Handbook for Pharmacists; Kenneth A Connors, ed.; John Wiley & Sons, New York, pp. 151-160; (1979).
Heart Guard; Product Information Sheet, "Emergency Aspirin Dispenser for Heart Attacks"; 2 pages; printed Dec. 19, 2018; http://dummypage2.tripod.com/.
International Search Report and Written Opinion for International Application PCT/EP2018/086213 International Filing Date: Dec. 20, 2018; dated Mar. 1, 2019; 15 pages.
International Search Report and Written Opinion for International Application PCT/EP2018/086260 International Filing Date: Dec. 20, 2018; dated Mar. 1, 2019; 14 pages.
International Search Report and Written Opinion, International Application No. PCT/EP2017/065970; International Filing Date Jun. 28, 2017; dated Sep. 29, 2017; 13 pages.
Javaid, K. et al.; "Dissolution of Aspirin from Tablets Containing Various Buffering Agents"; Journal of Pharmaceutical Sciences, vol. 61, Issue No. 9; 1972; pp. 1370-1373.
NO 20161073 filed Jun. 28, 2016, NO Search Report, 2 pages.
WHO; "Key Facts"; Cardiovascular Diseases (CVDs); printed Mar. 22, 2019; 6 pages; www.who.int/en/news-room/fact-sheets/detail/cardiovascular-diseases-(cvds).
WHO; "On World Heart Day WO Calls for Accelerated Action to Prevent the World's Global Killer"; printed Mar. 22, 2019; 3 pages; www.who.int/cardiovascular_diseases/en/.
Anonymous: Google Search for "solution of aspirin for heart attack," [conducted Jan. 28, 2022]; 2022; 2 pages.
Gilani, N.; "What Is Sodium Lauryl Sulfate?"; available online at [https://sciencing.com/sodium-lauryl-sulfate-6320871.html] retrieved on May 17, 2022; 2017; 5 pages.
Giordano, F. et al.; "Physical Properties of Parabens and Their Mixtures: Solubility in Water, Thermal Behavior, and Crystal Structures"; Journal of Pharmaceutical Sciences, vol. 88, Issue No. 11; 1999; pp. 1210-1216.

(Continued)

*Primary Examiner* — Michael Barker
(74) *Attorney, Agent, or Firm* — Karen A. LeCuyer; DeWitt LLP

(57) ABSTRACT

The present invention relates to a novel two-component system comprising acetylsalicylic acid (ASA) and which is particularly useful in providing an aqueous solution of ASA for immediate peroral administration.

12 Claims, No Drawings

(56) References Cited

OTHER PUBLICATIONS

Anonymous; "FDA Will Discuss Professional Aspirin Labeling"; Pink Sheet, available online at https://pink.pharmaintelligence.informa.com/PS015961/FDA-WILL-DISCUSS-PROFESSIONAL-ASPIRIN-LABELING [retrieved May 19, 2021]; 1989; 1 page.
Anonymous; "Heart Attack (Myocardial infarction)"; available online at my.clevelandclinic.org/health/diseases/16818-heart-attack-myocardial-infarction (p. 1); retrieved on May 19, 2021; 1 page.
Anonymous; "Use of Aspirin for Primary Prevention of Heart Attack and Stroke"; Food and Drug Administration 'Pink Sheet'; available online at www.fda.gov/drugs/information-consumers-and-patients-drugs/use-primary-prevention-heart-attack-and-stroke; 1989; 3 pages.
Dressman, J. et al.; "Biowaiver Monograph for Immediate-Release SOlid Oral Dosage Forms: Acetylsalicylic Acid" Journal of Pharmaceutical Sciences, vol. 101, Issue No. 8; 2012; pp. 2653-2657.
Xian, Y Ed. et al.; "Health Education Prescription of Common Clinical Diseases"; Changjiang Publishing & Media, Hubei Science and Technology Press; 2015; 5 pages.
Anonymous; "Background review for sodium laurylsulfate used as an excipient"; European Medicines Agency, Committee for Human Medicinal Products (CHMP), EMA/CHMP/351898/2014; 2015; 18 pages.
Anonymous; "Food Additive Status List"; Food and Drug Administration, available online at www.fda.gov/food/food-additives-petitions/food-additive-status-list, retrieved Sep. 19, 2022; 8 pages.
Rowe, et al. (Ed ); "Sodium Lauryl Sulfate"; Handbook of Pharmaceutical Excipients, Fifth Edition; Pharmaceutical Press, London, UK; 2006; pp. 1-5 and 687-689.
Anonymous; "Phosphate Buffer Calculator"; available online at https://web.archive.org/web/20160229074141/http://clymer.altervista.org/buffers/phos.html [downloaded Aug. 31, 2021]; 2016; 2 pages.
Anonymous; "Trisodium Phosphate"; Wikipedia, available online via the Wayback Machine at "https://web.archive.org/web/20161013211737/https://en.wikipedia.org/wiki/Trisodium_phosphate" [retrieved Aug. 31, 2021]; 2016; 6 pages.
Google Patent Search; "kit comprising aspirin and buffer solution"; patents.google.com, captured Aug. 31, 2021; https://www.google.com/search?q=kit+comprising+aspirin+and+buffer+solution&biw=15; 2021; 2 pages.
Google Patent Search; "two compailment package for incompatible chemicals liquid powder"; patents.google.com, captured Aug. 31, 2021; https://patents.google.com/?q=two+compartment+package+incompatible+chemicals+liquid+powder; 2021; 2 pages.
Google Scholar Search; "Stability of Aspirin in Phosphate Buffer"; scholar.google.com, captured Aug. 30, 2021; https://scholar.google.com/scholar?hl=en&as sdt=0%2C47&q=stability+of+aspirin+in+phosphate+buffer&btnG=; 2021; 2 pages.
Google Search; "two component aspirin phosphate buffer solution"; google.com, captured Aug. 30, 2021; https://www.google.com/search?q=two+component+aspirin+phosphate+buffer+solution; 2021; 2 pages.
Jordan, J. et al.; "pH of Trisodium Citrate Solutions Stored under Customary Laboratory Conditions"; Nature, vol. 161, Issue No. 4085; 1948; pp. 240-241.
Ambros, M. et al.; "Citric Acid: A Multifunctional Pharmaceutical Excipient"; Pharmaceutics, vol. 14, Issue No. 5, Article 972; 2022; 18 pages; DOI: https://doi.org/10.3390/pharmaceutics14050972.
Macleman, E.; "Propylparaben: Is It Safe to Use?"; The Dermatology Review, available online at "https://thedermreview.com/propylparaben/" retrieved on Dec. 6, 2022; 19 pages.
Palkin, J. et al.; "Aspirin"; Circulation, vol. 125, Issue No. 10; 2012; pp. e439-e442.
Pereira, B. et al.; "Benzalkonium Chlorides: Uses, Regulatory Status, and Microbial Resistance"; Applied and Environmental Microbiology, vol. 85, Issue No. 13; 2019; 13 pages; DOI: 10.1128/AEM.00377-19.
Aulton, M. et al. (Ed.); "Aulton's Pharmaceutics: The Design and Manufacture of Medicines"; Elsevier Ltd., Edinburgh; 2013; pp. 306-309.
Nitelius, E. et al.; "Actions and Interactions of Acetylsalicylic Acid, Salicylic Acid and Diflunisal on Platelet Aggregation"; European Journal of Clinical Pharmacology, vol. 27; 1984; pp. 165-168.
Rowland, M. et al.; "Absorption Kinetics of Aspirin in Man following Oral Administration of an Aqueous Solution"; Journal of Pharmaceutical Sciences, vol. 61, Issue No. 3; 1972; pp. 379-385; DOI: 10.1002/jps.2600610312.

TWO COMPONENT COMPOSITIONS

CROSS REFERENCE TO RELATED APPLICATIONS

This application is a National Stage application of PCT/EP2018/086260, filed Dec. 20, 2018, which claims the benefit of priority to European Patent Application No. 17210437.4, filed Dec. 22, 2017, both of which are incorporated by reference in their entirety herein.

The present invention relates to a new two-component composition or system useful in the treatment and prevention of imminent myocardial infarction. In particular, the invention relates to a pharmaceutical two-component system, comprising a first component and a second component, wherein the first component comprises acetylsalicylic acid (ASA), and the second component comprises an aqueous solution comprising a salt of carbonic acid. Furthermore, a salt of sorbic acid and/or a salt of benzoic acid can be comprised in the first component and/or in the second component. The two-component system enables an immediate dissolution of ASA upon mixing of the first and second components of the present two-component system, and is in particular useful in the treatment of imminent myocardial infarction. The present two-component system is in particular useful as a first aid treatment of patients in need for immediate administration of ASA in order to avoid the development of a heart attack, or reduce the extent of damage of a heart attack.

BACKGROUND OF THE INVENTION

Cardiovascular diseases are one of the leading causes of mortality and morbidity in the western world. According to the World Health Organization cardiovascular diseases are the number one cause of death globally, and it is estimated that 17.5 million people die every year from cardiovascular disease, estimated to about 31% of all deaths worldwide. Furthermore, 80% of all deaths by cardiovascular diseases are caused by hearth attacks or strokes (cf. http://www.who.int/cardiovascular_diseases/en/ and http://www.who.int/mediacentre/factsheets/fs317/en/).

Although numerous medicinal agents are available for the treatment of the various cardiovascular diseases, such as e.g. cholesterol reducing drugs, numerous medicines aiming at reducing blood pressure, blood thinners, etc., patients with cardiovascular diseases are still at high risk of premature death.

A myocardial infarction (heart attack) is usually heralded by harbingers, i.e., warning signs occurring in advance, making it possible to take action and thus avoid or reduce the serious consequences of a myocardial infarction.

It is well known that chance of survival of patients experiencing symptoms of a myocardial infarction increase significantly if the patients receive ASA as quickly as possible, preferably immediately. Quick administration of ASA is thus crucial in order to avoid death and to reduce damage to the cardiovascular system. To ensure quick absorption and high bioavailability, ASA must be dissolved at the time of administration. ASA however has a poor solubility rendering it difficult to provide an aqueous ASA solution quickly. Further, ASA and salts of ASA hydrolyse rapidly in water (Connors et al., Chemical stability of Pharmaceuticals, A Handbook for Pharmacists, pages 151-160), so it is not possible to store dissolved ASA over time.

Hence, in order to successfully treat an upcoming myocardial infarction, a patient needs to have ASA available in a form that can be dissolved and administered (swallowed) very quickly and without need of additional water or adequate saliva production.

As of today, effervescent tablets containing ASA are commonly used as immediate treatment of patients experiencing symptoms of a heart attack. A product commonly used for this purpose is, e.g. Dispril®, an effervescent tablet containing 300 mg acetylsalicylic acid.

Effervescent formulations in general, as well as those containing ASA, commonly comprise effervescent agents, such as an acid source together with a type of carbonate or hydrogen carbonate, such as sodium hydrogen carbonate or calcium carbonate.

Prior to the administration of the effervescent tablets, the tablets must be dissolved in water, or dissolved in saliva in the mouth of the patient. This might take several minutes, typically 5 minutes.

WO2015/061521 discloses an effervescent tablet comprising high levels of ASA and an alkaline substance (e.g. sodium hydrogen carbonate), and vitamin C.

EP1428525 discloses a pharmaceutical preparation for veterinary use containing ASA in the form of a buffered powder. Said powder still necessitates water in order to dissolve the powder, and will thus not solve the problem of needing to have a glass of water available.

US20120316140 A1 describes a soluble aspirin (=ASA) composition, wherein the soluble aspirin (ASA) composition when introduced to water undergoes a reaction. This reaction triggers effervescing action and the disintegration of the ASA granules which rapidly dissolve in the water.

U.S. Pat. No. 5,776,431 A discloses water-soluble aspirin compositions comprising aspirin, potassium citrate (tri) monohydrate or sodium citrate (tri) dihydrate, and a surface-active agent (e.g. sodium lauryl sulfate). Such a composition comprising 500 mg aspirin is dissolved in 150 ml water.

Multi-compartment capsules comprising different chambers for ingredients with different physical states have been described in US2005008690 A1 and EP2777802 A1. A successful incorporation of ASA into such a capsule is however not disclosed in said document.

The drawbacks with the prior art tablets and capsules are that the patients need to have a glass of water accessible in order to dissolve the tablets, and that the complete dissolution time may take several minutes. Thus, the prior art tablets are not optimal for quickly administration of ASA, i.e. said tablet are not optimal for increasing the change of survival of patients experiencing symptoms of a myocardial infarction.

Furthermore, a patient experiencing signs of an imminent (i.e., developing) myocardial infarction usually has reduced or deficient saliva production, resulting in a dry mouth. Reduced or deficient saliva production is hampering dissolution of an oral tablet containing ASA. It is therefore crucial that the patient has liquid readily available in order to dissolve and/or ingest ASA.

Also, chewable tablets containing ASA are available as immediate treatment of patients experiencing symptoms of a heart attack. However, for the same reason as mentioned above, also the dissolution of and release of ASA from a chewable tablet is often hampered by the reduced or deficient salvia production in the patients.

Taken together, even though products containing ASA for emergency use are available (see, e.g., http://dummypage2.tripod.com/index.htm#origin), such products will be inadequate in lack of water or poor saliva production.

WO2017001468 discloses a two-component composition comprising aspirin and a carbonate in one component and a dissolution solution with a surfactant in the other component. However, in retrospect the applicant has realized that this solution wasn't optimal.

Therefore, there is still a need for an ASA formulation or system suitable for quickly providing an aqueous solution comprising ASA that may be administered to patients in need for urgent treatment of an imminent myocardial infarction. In particular, there is a need for an ASA formulation that avoids the need of additional water or adequate saliva production in a given patient in order for the ASA to be administered and taken up quickly.

SUMMARY OF THE INVENTION

The present inventor has found that a stable ASA formulation can be provided with a two-component system comprising the active ingredient ASA in a first compartment and an aqueous solution of carbonic acid in the second compartment, which upon mixing of the content of the two compartments quickly provides an aqueous solution of ASA that may be administered to or taken by a patient in need thereof. The present inventors have also found that a salt of sorbic acid and/or benzoic acid can be comprised in either the first component together with ASA or in the second component together with the salt of carbonic acid or in both the first and in the second component. Such solution also provides quickly aqueous solution of ASA, but with a lower final pH.

In particular, the present invention provides a two-component system comprising a first and a second component which are physically separated, wherein the first component comprises a therapeutically effective amount of acetylsalicylic acid (ASA) and optionally one or more pharmaceutically acceptable excipients; and wherein the second component comprises an aqueous solution comprising at least one pharmaceutically acceptable salt of carbonic acid and optionally one or more pharmaceutically acceptable excipients; provided that the second component does not comprises a salt of citric acid; and wherein an aqueous solution of ASA with a pH above approx. 7.5 will be obtained upon mixing of the two components.

According to one aspect, a two-component system is provided comprising a first and a second component which are physically separated, wherein the first component comprises a therapeutically effective amount of acetylsalicylic acid (ASA), and optionally one or more pharmaceutically acceptable excipients; and wherein the second component consist of an aqueous solution of at least one pharmaceutically acceptable salt of carbonic acid.

In particular, the present invention provides a two-component system comprising a first and a second component which are physically separated, wherein the first component comprises a therapeutically effective amount of acetylsalicylic acid (ASA) and optionally one or more pharmaceutically acceptable excipients; and wherein the second component comprises an aqueous solution comprising at least one pharmaceutically acceptable salt of carbonic acid and optionally one or more pharmaceutically acceptable excipients; provided that the second component does not comprises a salt of citric acid, lactic acid, ascorbic acid, malonic acid, succinic acid, and/or glutaric acid; and wherein an aqueous solution of ASA with a pH above approx. 7.5 will be obtained upon mixing of the two components.

The present invention furthermore comprises two-component system comprising a first and a second component which are physically separated, wherein the first component comprises a therapeutically effective amount of acetylsalicylic acid (ASA), at least one pharmaceutically acceptable salts of an acid selected from the group consisting of sorbic acid and/or benzoic acid, and optionally one or more pharmaceutically acceptable excipients; and wherein the second component comprises an aqueous solution comprising at least one pharmaceutically acceptable salt of carbonic acid and optionally one or more pharmaceutically acceptable excipients; and wherein an aqueous solution of ASA with a pH above approx. 7.5 will be obtained upon mixing of the two components.

The present invention furthermore comprises two-component system comprising a first and a second component which are physically separated, wherein the first component comprises a therapeutically effective amount of acetylsalicylic acid (ASA) and optionally one or more pharmaceutically acceptable excipients; and wherein the second component comprises an aqueous solution comprising at least one pharmaceutically acceptable salt of carbonic acid, at least one pharmaceutically acceptable salt of an acid selected from the group consisting of sorbic acid and/or benzoic acid, and optionally one or more pharmaceutically acceptable excipients; and wherein an aqueous solution of ASA with a pH above approx. 7.5 will be obtained upon mixing of the two components.

According to one aspect, said salts of an acid selected from the group consisting of sorbic acid and/or benzoic acid is comprised in both the first and in the second component.

When a salt of sorbic acid and/or benzoic acid is comprised in the first component together with ASA, it is to be understood that the salt of sorbic acid and/or benzoic acid is present in solid form, such as a powder.

According to one aspect, the pH obtained after dissolution of ASA in the second component is above approx. 8, such as a pH of approx. 8.5, 9, 9.5, or 10.

According to one aspect, the salt of carbonic acid is selected from the group consisting of sodium carbonate and potassium carbonate.

According to one aspects, the salt of sorbic acid is potassium sorbate and the salt of benzoic acid is sodium benzoate.

According to yet another aspect, a two-component system is provided wherein the first component comprises ASA in the range of 100-600 mg, such as 100 mg, 200 mg, 300 mg, 400 mg, 500 mg or 600 mg.

According to yet another aspect of the invention, the volume of the aqueous solution of the second component is in the range of 6 ml 50 ml. According to one aspect, the volume of the second component is in the range of 8-15 ml.

In one aspect, the two-component system according to the invention comprises 300-325 mg ASA in the first component and wherein the volume of the second component is in the range of 8-15 ml.

According to yet another aspect of the present invention, the two-component system consist of a first and a second component, wherein the first component consist of a therapeutically effective amount of acetylsalicylic acid (ASA); and wherein the second component consist of an aqueous solution of at least one pharmaceutically acceptable salt of carbonic acid; and wherein the pH obtained after dissolution of ASA in the second component is above approx. 7.5.

According to yet another aspect of the present invention, the two-component system consist of a first and a second component, wherein the first component consist of a therapeutically effective amount of acetylsalicylic acid (ASA); and wherein the second component consist of an aqueous solution of at least one pharmaceutically acceptable salt of carbonic acid; and wherein at least one pharmaceutically acceptable salt of an acid selected from the group consisting of sorbic acid and/or benzoic acid is comprised in either the first component together with ASA or in the second component together with the salt of carbonic acid or in both the first and in the second component; and wherein the pH obtained after dissolution of ASA in the second component is above approx. 7.5. The present invention furthermore provides a two-component system according to the present invention for use in the treatment of imminent myocardial infarction. According to one aspect, the first component comprising ASA is dissolved in the second component comprising the aqueous solution, thus providing a ready-to-use aqueous solution of acetylsalicylic acid ASA prior to administration.

According to yet another aspect of the invention, said ready-to-use aqueous solution of ASA is obtained within approx. one minute or less. In yet another aspect, said ready-to-use aqueous solution is obtained within approx. 40 sec. or less. In yet another aspect, said ready-to-use aqueous solution of ASA is obtained within approx. 25-30 sec. or less. According to yet another aspect, said ready-to-use aqueous solution of ASA is obtained within approx. 10-15 sec.

Furthermore, the present invention provides a container comprising a first and a second chamber, wherein the first chamber comprises a therapeutically effective amount of ASA and optionally one or more pharmaceutically acceptable excipients; and wherein the second chamber comprises an aqueous solution comprising at least one pharmaceutically acceptable salt of carbonic acid and optionally one or more pharmaceutically acceptable excipient; provided that the second chamber does not comprises a salt of citric acid; and wherein an aqueous solution of ASA with a pH above approx. 7.5 will be obtained upon mixing of the content of the two chambers.

Furthermore, the present invention provides a container comprising a first and a second chamber, wherein the first chamber comprises a therapeutically effective amount of ASA and optionally one or more pharmaceutically acceptable excipients; and wherein the second chamber comprises an aqueous solution comprising at least one pharmaceutically acceptable salt of carbonic acid and optionally one or more pharmaceutically acceptable excipient; and wherein at least one pharmaceutically acceptable salt of an acid selected from the group consisting of sorbic acid and/or benzoic acid is comprised in either the first chamber together with ASA or in the second chamber together with the salt of carbonic acid or in both the first and in the second chamber; and wherein an aqueous solution of ASA with a pH above approx. 7.5 will be obtained upon mixing of the content of the two chambers.

According to yet an aspect of the present container, the pH obtained after dissolution of ASA in the second component is above approx. 8.

According to yet an aspect of the present container, the salt of carbonic acid is selected from the group consisting of sodium carbonate and potassium carbonate.

According to yet an aspect of the present container, the salt of sorbic acid is potassium sorbate and the salt of benzoic acid is sodium benzoate.

Finally, the present invention provides a method for treating imminent myocardial infarction by administering an aqueous solution of ASA to a patient in need thereof, said method comprising the steps of:

a) providing a two-component system or container comprising a first and a second component/chamber according to the present invention;

b) mixing the content of the first component/chamber with the aqueous solution of the second component/chamber, thus obtaining an aqueous solution of ASA;

c) administering to the person in need thereof the mixture obtained in step b).

According to one aspect, a method is provided, wherein the aqueous solution of ASA obtained in step b) is provided within about one minute or less, such as within about 40 sec. or less.

According to another aspect of the present method, an aqueous solution of ASA is obtained within about 25-30 sec.

Definitions

The term "cardiovascular disease" as used herein refers to diseases where the patients suffering from the cardiovascular disease is in risk of having a heart attack. In particular, "cardiovascular diseases" as used herein includes ischemic heart disease, congestive heart failure, hypertension, valvular heart disease, general atherosclerosis, hypercholesterolemia, etc. The spectrum of ischemic heart disease comprised stable and unstable angina and acute myocardial infarction, conditions usually treated either by pharmacology or by coronary revascularization. Revascularization procedures can be done either catheter-based, or by coronary artery bypass grafting.

The product of the present invention is applicable in the treatment of imminent acute myocardial infarction, where the terms "myocardial infarction" and "heart attack" are used interchangeably herein.

The terms "treating" or "treat" as used herein refers to reduction in severity and/or reduction of the further development of a heart attack, and improvement or amelioration of damage that may be caused by a heart attack.

Patients diagnosed with any of the indications listed above may risk developing a heart attack or experiencing symptoms or warnings of a heart attack being imminent. The terms "treatment", "treating" or "treat" as used herein in accordance with the present invention refers to treatment of patients diagnosed with a cardiovascular disease as defined above, and which are in need of ASA due to the occurrence of imminent acute myocardial infarction.

The terms "aspirin" or "acetylsalicylic acid" or "ASA" are used interchangeably herein.

The term "component" as used herein in respect of the first and second component of the present two-component system refers herein to a component comprising at least one ingredient or compound, and which may also be a mixture of different ingredients or compounds. This is evident from the herein description of the first and the second component of the present invention, e.g. from the fact that the first component comprises ASA and optionally one or more pharmaceutically acceptable excipients; and that the second component comprises an aqueous solution comprising at least one pharmaceutically acceptable salt of carbonic acid and optionally one or more a pharmaceutically acceptable excipient. Furthermore, a salt of sorbic acid and/or a salt of benzoic acid can be comprised in the first component together with ASA and/or in the second component together with carbonate or in both components. It is thus to be understood that the first component comprises a composition comprising ASA and optionally one or more pharmaceutically acceptable excipients.

The term "two-component system" as used herein refers to a product comprising at least two compositions which are kept apart prior to administration, and which are to be mixed in order to provide a ready-to-use solution to be administered to patients in need thereof.

The term "pH regulating agent" or "acidity regulating agents" as used herein refers to a compound added to the first or the second component of the present system in order to change or maintain the pH of the components.

The term "preservative" as used herein refers to a substance or a chemical commonly added to pharmaceutical composition in order to prevent microbial growth or decomposition or undesired chemical changes to a product.

The term "sweetening agent" as used herein refers to compounds commonly added to pharmaceutical composition in order to sweeten or mask an unpleasant taste caused by the active ingredient or any of the excipients used in the composition.

The term "flavoring agent" as used herein refers to compounds commonly added to pharmaceutical composition in order to provide a pleasant taste and/or mask an unpleasant taste caused by the active ingredient or any of the excipients used in the composition.

DETAILED DESCRIPTION OF THE INVENTION

For patients having a heart attack or experiencing symptoms or warnings of a heart attack being imminent, it is shown that administration of ASA taken as soon as possible increases the chances of survival and reduces the risks of developing damage to the cardiovascular system and the heart. The appropriate dosage of ASA for such use is found to be 300 mg, which correspond to the amount of active ingredient in the effervescent tablet Dispril®, cf. Elwood et al, 2001, The Pharmaceutical Journal, 266:315. The Dispril® tablets comprise calcium carbonate, corn starch, citric acid, talk, saccharine and sodium lauryl sulphate (http://slv.no/_layouts/Preparatomtaler/Spc/0000-02602.pdf).

The problem with the standard prior art tablets containing ASA such as, e.g. Dispril®, is that they firstly must be dissolved in water, and thus necessitate that a glass of water be available whenever needed. In addition, the lack of saliva in the mouth in patients suffering from an imminent heart attack, for reasons of acute fear and adrenergic reactions, results in the patients having trouble to dissolve tablets in their mouth. In both scenarios, this results in the need of water, which is a drawback for swift administration. In addition, the time taken for the prior art tablets to be dissolved, results in the fact that the patients in need of immediate administration of ASA are not provided with said medication quickly enough.

The present invention solves this problem by providing a product that ensures rapid dissolution of ASA and provides a solution that can be quickly administered to the patient, independent of whether a glass of water is available or not and independent of saliva production of the patient.

Acetylsalicylic acid (ASA) is commonly known as aspirin, having the following structure:

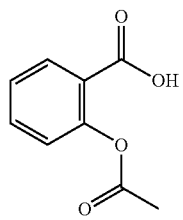

ASA is assigned the CAS Registry number 50-78-2. Aspirin is used in the treatment of numerous conditions, e.g. as analgesic, in treatment of inflammatory disorder, cardiovascular disorder etc. In particular, it is used in order to reduce the risk of death from heart attack. ASA however has poor water solubility, and the low solubility of ASA renders it difficult to quickly provide a solution to be administered immediately when a patient experiences symptoms of having a heart attack. In standard pharmaceutical compositions, ASA is rearranged to a soluble salt upon dissolution of the composition in order to improve solubility. Both ASA and the salt of ASA are unstable in aqueous solutions and will quickly hydrolyse forming salicylic acid and acetic acid (Connors et al., Chemical stability of Pharmaceuticals, A Handbook for Pharmacists, pages 151-160).

The present invention provides a two-component system comprising separately i) a first component comprising ASA and optionally one or more pharmaceutically acceptable excipients; and ii) a second component comprising an aqueous solution comprising a pharmaceutically acceptable salt of carbonic acid and optionally one or more pharmaceutically acceptable excipients; and eventually iii) a pharmaceutically acceptable salt of sorbic acid and/or benzoic acid comprised in either the first component or in the second component or in both the first and in the second component. Further, the salt of carbonic acid is selected from the group consisting of sodium carbonate ($Na_2CO_3$) or potassium carbonate ($K_2CO_3$), the salts of sorbic acid and benzoic acid is selected from the group consisting of potassium sorbate and sodium benzoate; and the pH obtained after dissolution of ASA in the second component is above approx. 7.5, such as above approx. 8 or above approx. 8.5, 9, 9.5, or 10.

The two-component system according to the present invention represents an improvement of emergency treatment of patients having an imminent heart attack, or being in the process of developing a heart attack, in that it provides:
- a ready to use solution comprising ASA,
- Immediate treatment of imminent myocardial infarction without the need of a glass of water,
- Immediate treatment of myocardial infarction independent of saliva production in a given patient,
- a ready to use emergency medicinal product that can be easily carried by a broad population, including patients in risk of developing heart attack as well as their relatives, or being available in first aid kits in private houses or public places as well as emergency rooms at medical practices and hospitals.

Although the present two-component system is in particular useful as an emergency care product for the treatment of heart attack, the skilled person will acknowledge that the two-component system may have other useful applications. E.g., aspirin is well known as a painkiller and an antipyretic agent. Thus, the two-component system of the present invention may also be used for the treatment or prevention of any other medical condition where administration of aspirin to a patient is desired.

According to the present invention, the ASA present in the first component/compartment is quickly dissolved when mixed or added to the aqueous solution comprised in the second component/compartment. The aqueous solution comprised in the second component or compartment of the present invention comprises a salt of carbonic acid. Furthermore, a salt of sorbic acid and/or benzoic acid can be comprised in the first component and/or in the second component According to one embodiment, the salt of sorbic acid is potassium sorbate, the salt of benzoic acid is sodium benzoate, and the salt of carbonic acid is sodium carbonate and/or potassium carbonate or a combination thereof.

The salt of sorbic acid, benzoic acid, and/or carbonic acid as used according to the present invention should provide the formation of an easily soluble acetylsalicylate, such as sodium acetylsalicylate or potassium acetylsalicylate. The aqueous solution of the salt of the carbonic acid and eventually the sorbic acid and/or benzoic acid should have sufficient buffer capacity in order to slow or counteract the pH reduction affected upon mixture with ASA.

According to one aspect, the pH of the aqueous solution of the second component of the present invention has a pH of above approx. 10 (before dissolution of ASA). In yet another aspect, the second component of the two-component system has a pH of about 11-11.6 (before dissolution of ASA).

Without being bound by theory, it is believed that ASA comprised in the first component when mixed with the second component becomes ionized contributing to the quick providing of a dissolution of ASA.

According to one aspect, the pH of the solution obtained upon mixing of the first and the second components of the present invention is approx. 10.

In yet another aspect, the solution obtained upon mixing of the first and the second component provides a solution of ASA having a pH in the range of approx. 8-8.5.

The final pH to be obtained after dissolution of ASA is in one aspect merely influenced by ASA and the salt of carbonic acid. In yet another aspect, the final pH to be obtained after dissolution of ASA is merely influenced by ASA, the salt of carbonic acid and the salt of sorbic acid, or merely by ASA and the salt of carbonic acid and the salt of benzoic acid, or merely by ASA and the salt of carbonic acid, the salt of sorbic acid and the salt of benzoic acid.

The desired pH of the aqueous solution of the second component may furthermore be obtained by including a suitable pH regulating agent.

A further aspect of the present invention is that the dissolution of ASA does not necessitate the use of a surfactant. According to one aspect of the present invention, the second component of the present two-component system comprises an aqueous solution optionally comprising one or more pharmaceutically acceptable excipients, provided that the one or more pharmaceutically acceptable excipient is not a surfactant.

A well know technique to increase the dissolution rate of a poorly soluble drug is micronization. When a drug is micronized the surface area of the drug is increased and the drug will thus dissolve more rapidly.

Thus, a further aspect of the present invention is to have micronize ASA in the first component. Micronization of drug can sometimes lead to aggregation. If aggregation of micronized ASA occurs, a surfactant can be added to the first component.

According to the present invention, the first component comprises a pharmaceutically acceptable amount of ASA. Said first component may comprise from 50 mg to 2000 mg ASA, such as 100 mg, 200 mg, 300 mg, 400 mg, 500 mg or 600 mg. For the purpose of treating imminent myocardial infarction or reducing the damages thereof, the first component of the present invention typically comprises from 300 to 325 mg of ASA.

The volume of the aqueous solution of the second component of the present two-component system depends upon the specific medical indication as well as the size of the device comprising separately the two-components of the system. Typically, the volume of the second aqueous solution of the second component is within the range 6-50 ml, such as from 6-40 ml, such as from 8-30 ml, such as from 8-20 ml, or any number in-between said ranges. According to one embodiment of the present invention, the volume of the aqueous solution of the second component is in the range of 8-15 ml. According to one embodiment, the volume of the aqueous solution is in the range of 10-12 ml.

According to one embodiment, the first component comprises from 100 mg to 600 mg, such as 100 mg, 200 mg, 300 mg, 400 mg, 500 mg or 600 mg ASA, which is to be dissolved in 6-50 ml of the aqueous solution of the second component of the present two-component system.

According to another embodiment, the first component comprises from 300 to 325 mg ASA, and the second component comprises from 8 to 15 ml of the aqueous solution.

According to yet another embodiment, the first component comprises from 300 to 325 mg ASA, and the second component comprises approx. 8 ml of the aqueous solution.

According to yet another embodiment, the first component comprises from 300 to 325 mg ASA, and the second component comprises approx. 9 ml of the aqueous solution.

According to yet another embodiment, the first component comprises from 300 to 325 mg ASA, and the second component comprises approx. 10 ml of the aqueous solution.

According to yet another embodiment, the first component comprises from 300 to 325 mg ASA, and the second component comprises approx. 11 ml of the aqueous solution.

According to yet another embodiment, the first component comprises from 300 to 325 mg ASA, and the second component comprises approx. 12 ml of the aqueous solution.

According to yet another embodiment, the first component comprises from 300 to 325 mg ASA, and the second component comprises approx. 13 ml of the aqueous solution.

According to yet another embodiment, the first component comprises from 300 to 325 mg ASA, and the second component comprises approx. 14 ml of the aqueous solution.

According to yet another embodiment, the first component comprises from 300 to 325 mg ASA, and the second component comprises approx. 15 ml of the aqueous solution.

The present first and/or second component of the present two-component system may optionally comprise further pharmaceutically acceptable excipients. For example, flavoring agents may be added in order to provide a pleasant taste and/or mask an unpleasant taste caused by the active ingredient or any of the excipients used in the system. Non-limiting examples of compounds that may be used for the purpose of providing a certain taste is e.g. peppermint essence or juice of fruit or berries, such as e.g. blackcurrant juice.

According to one aspect, a flavoring agent is added to the second component of the present two-component system. For example, peppermint essence may be added to the second component of the present system, such as, e.g., in the amounts of about 1% (v/v) of the amount of the second component. Alternatively, blackcurrant juice may be added to the second component of the present system, such as e.g. in the amount of 20% (v/v) of the amount of the second component. Blackcurrant juice may also act as a pH regulating agent.

The present two-component system may furthermore include sweetening agents in order to improve taste or mask unpleasant taste of the other ingredients in the system. The skilled person is well known with various sweetening agents commonly used as sweetening agents in pharmaceutical composition. A non-limiting example of a sweetening agent that may be used in respect of the present invention is saccharine sodium. Saccharine sodium may be added to the second component of the present system, such as, e.g., in the amounts of approx. 0.03 to 0.06% (w/v) of the amount of second component.

The two-component system included in the present invention may be administered to the patient in need thereof using a device, capsule or container comprising said first component and the second component in separate departments or chambers of a device, capsule or container. A predetermined amount of the first component and predetermined amount the second component, will upon operation of the device, capsule or container be mixed and immediately form a ready-to-use solution of dissolved ASA to be taken by or administered to the patient in need thereof.

For example, a container or capsule for segregated storage of two-component miscible substances as disclosed in WO00/66456 may be used in connection with the present invention for the treatment or prevention of myocardial infarction.

A package for keeping products separated before used as disclosed in WO98/38104 may also be applied for the purpose of present invention.

The skilled person will understand that a device, package, capsule or container for segregated storage of two-component miscible substances, such as a first component comprising a dry powder comprising ASA and a second component comprising a dissolution solution according to the present invention, may be designed in various ways. It is to be understood that the two-component system according to the present invention may be placed in any capsule, container, package or device that will provide immediate dissolution of the ASA comprised in the first component upon mixing with the dissolution solution of the second component irrespective of the exact design of the capsule, container, package or device the two-components may be placed in as long as the two-components are separated during storage and prior to use.

The volume of the chamber of the capsule, container or storage device to be used with the present second component of the two-component system is in size suitable for storage of an aqueous solution enabling the dissolution of the desired amount of ASA in accordance with the present invention. Similarly, the volume of the chamber of the capsule, container or storage device to be used with the present first component of the two-component system of the present invention is in size suitable for storage of the desired amount of the first component.

EXAMPLES

Example 1 Preparation of Two-Component System, Dissolution of ASA in Aqueous Solutions of Salts of Carbonic Acid Three aqueous solutions of sodium carbonate ($Na_2CO_3$) were prepared by dissolving and mixing sodium carbonate in water in the concentrations listed in table 1.

TABLE 1

| Carbonate solution 1, 2, and 3 | |
|---|---|
| Carbonate solution 1 | 100 ml 0.33 Molar $Na_2CO_3$ (35 mg/ml $Na_2CO_3$) |
| Carbonate solution 2 | 100 ml 0.22 Molar $Na_2CO_3$ (23.3 mg/ml $Na_2CO_3$) |
| Carbonate solution 3 | 100 ml 0.11 Molar $Na_2CO_3$ (11.7 mg/ml $Na_2CO_3$) |

An obvious alternative to the above three sodium carbonate solutions is aqueous solutions of potassium carbonate ($K_2CO_3$). Sodium and potassium is equal cations which do not affect pH. Thus, the present experiment with sodium carbonate is representative for both sodium carbonate solutions as well as for potassium carbonate solutions.

A device as disclosed in WO98/38104 provided by Bormioli Rocco S.p.A., Italy was used for the purpose of testing the dissolution characteristics of ASA in the above carbonate solutions.

15 ml of the sodium carbonate solutions were filled into the container (bottle) of the test device (3 phase kit with PET bottle, Bormioli Rocco S.p.A., Italy). 300 mg ASA was then placed in the powder compartment of the device. The cap comprising the powder compartment and the cutting element was assembled with the container comprising the solution.

The cap was then turned down until the seal keeping the powder and the solution separately was broken by the cutting element. The cutting of the seal resulted in that the ASA contained in the powder compartment was released into the solution in the container. The device was then shaken until all ASA was dissolved.

The results of the above testing, and the concentrations of the carbonate tested, are shown in table 2.

TABLE 2

Dissolution of 300 mg ASA in 15 ml of the carbonate solutions tested in said two-component device.

| | pH of the solution before dissolution of ASA | Time for dissolution of 300 mg ASA in 15 ml carbonate solution | pH of the solutions after dissolution of ASA |
|---|---|---|---|
| Carbonate solution 1 (0.33M) | 11.53 | within 10-15 sec. | 10.03 |
| Carbonate solution 2 (0.22M) | 11.51 | within 30 sec. | 9.83 |
| Carbonate solution 3 (0.11M) | 11.43 | within 60 sec. | 7.96 |

It is seen from the results presented in table 2 that an aqueous solution of carbonate can be used to provide a fast dissolution of ASA. In particular, the results show that the carbonate solutions 1 and 2 provide very fast dissolution of ASA.

The relatively high pH of the final solution is not a problem with regard to the stability of ASA since the solution has to be consumed immediately after dissolution.

Example 2 Dissolution of ASA in a Carbonate Solution that Further Comprises Salts of Sorbic Acid or Salts of Benzoic Acid The following aqueous solutions were prepared by dissolving and mixing sodium benzoate ($NaC_7H_5O_2$, Na-benzoate), potassium sorbate ($C_6H_7KO_2$, K-sorbate), and sodium carbonate ($Na_2CO_3$) in water. The concentrations Na-benzoate and K-sorbate and the amount of carbonate is listed in table 3.

TABLE 3 solutions of carbonate together with benzoate or together with sorbate

| | |
|---|---|
| Na-benzoate + carbonate solution | 15 ml Na-benzoate 0.33 Molar (47.6 mg/ml) + 175 mg $Na_2CO_3$ |
| K-sorbate + carbonate solution | 15 ml K-sorbate 0.33 Molar (49.5 mg/ml) + 175 mg $Na_2CO_3$ |

The device used in example 1 (disclosed in WO98/38104 provided by Bormioli Rocco S.p.A., Italy) was used as described in example 1 for the testing of the dissolution characteristics of ASA in the above carbonate, benzoate and sorbate solutions listed in table 3. The results of said tests are shown in table 4.

TABLE 4

Dissolution of 300 mg ASA in 15 ml of Na-benzoate + carbonate solution or in 15 ml of K-sorbate + carbonate solution tested in said two component device

| | pH of the solution before dissolution of ASA | Time for dissolution of 300 mg ASA in 15 ml carbonate solution | pH of the solutions after dissolution of ASA |
|---|---|---|---|
| Na-benzoate + carbonate solution | 11.30 | within 30-40 sec. | 7.98 |
| K-sorbate + carbonate solution | 11.53 | within 25-30 sec. | 8.43 |

It is seen from the results presented in table 2 that aqueous solutions of carbonate and benzoate and of carbonate and sorbate can be used to provide a fast dissolution of ASA.

Example 3 Dissolution of ASA and Salts of Either Sorbic Acid or Benzoic Acid in an Aqueous Carbonate Solution In the following example 300 mg ASA and a salt of either benzoic acid or of sorbic acid is dissolved at the same time in 15 ml carbonate solution.

300 mg of the ASA and 240 mg of the Na-benzoate were placed in the powder compartment of the test device used in example 1 (disclosed in WO98/38104 provided by Bormioli Rocco S.p.A., Italy), and 15 ml of the carbonate solution 1 (0.33 M) (see table 1) was filled into the container (bottle) of the device. The device was then used as described in example 1 for the testing of the dissolution characteristics of ASA and Na-benzoate in the carbonate solution. The result of said test is shown in table 5.

TABLE 5

Dissolution of ASA and Na-benzoate in 15 ml carbonate solution tested in said two component device

| | pH of the solution before dissolution of ASA | Time for dissolution of 300 mg ASA and 240 mg Na-benzoate in 15 ml carbonate solution | pH of the solutions after dissolution of ASA |
|---|---|---|---|
| Carbonate solution 1 (0.33M) | 11.53 | within 25 sec. | 9.95 |

It is seen from the results presented in table 5 that aqueous solutions of carbonate and benzoate, wherein benzoate before dissolution is comprised together with ASA, can be used to provide a fast dissolution of ASA.

Then, 300 mg of the ASA and 250 mg of the K-sorbate were placed in the powder compartment of the test device used in example 1 (disclosed in WO98/38104 provided by Bormioli Rocco S.p.A., Italy), and 15 ml of the carbonate solution 1 (0.33 M) (see table 1) was filled into the container (bottle) of the device. The device was then used as described in example 1 for the testing of the dissolution characteristics of ASA and K-sorbate in the carbonate solution. The result of said test is shown in table 6.

TABLE 6

Dissolution of ASA and K-sorbate in 15 ml carbonate solution tested in said two component device

| | pH of the solution before dissolution of ASA | Time for dissolution of 300 mg ASA and 250 mg K-sorbate in 15 ml carbonate solution | pH of the solutions after dissolution of ASA |
|---|---|---|---|
| Carbonate solution 1 (0.33M) | 11.53 | within 25-30 sec. | 9.97 |

It is seen from the results presented in table 6 that aqueous solutions of carbonate and sorbate, wherein sorbate before dissolution is comprised together with ASA, can be used to provide a fast dissolution of ASA.

Example 4 Calculations of Alternative Carbonate+Benzoate and Carbonate+Sorbate Solutions Based on the Final pH Values to be Obtained Alternative solutions of carbonate, sorbate and benzoate can be prepared for fast dissolution of ASA based on the knowledge of the final pH to be obtained, i.e. the pH in the final ASA solution that are to be taken by the patient.

Thus, for example if a final pH of 9 is to be obtained after dissolution of 300 mg ASA the amount (mg) of carbonate to be used in the second component is easily calculated based on said final pH to be obtained.

In such calculations, general knowledge of $pK_a$ and molar mass (M) is used.

In general, the pH in a hydrogencarbonate/carbonate buffer can be expressed as $$pH = pK_a + \log(n[CO_3^{2-}]/n[HCO_3^-]) \quad \text{Equation 1}$$

where $pK_a = -\log(K_a)$ for $HCO_3^- = 10.3$, $n[CO_3^{2-}]$=number of moles of $CO_3^{2-}$ and $n[HCO_3^-]$=number of moles of $HCO_3^-$.

If the desired pH is 9.0, substitution gives $$9.0 = 10.3 + \log \log(n[CO_3^{2-}]/n[HCO_3^-]) \quad \text{Equation 2}$$

$$\log(n[CO_3^{2-}]/n[HCO_3^-]) = -1.3 \quad \text{Equation 3}$$

$$n[CO_3^{2-}]/n[HCO_3^-] = 0.05 \quad \text{Equation 4}$$

$$n[CO_3^{2-}] = 0.05 n[HCO_3^-] \quad \text{Equation 5}$$

where all mole numbers refer to what is in solution after chemical reaction.

From the reaction $$ASA + CO_3^{2-} \rightarrow ASA^- + HCO_3^-$$

it follows that $$n(ASA)^0 = n[HCO_3^-] \quad \text{Equation 6}$$

where $n(ASA)^0$, the starting number of moles of ASA is 0.00167 for an amount of 300 mg (Mw=180.16 g/mol). From the mass balance $$n[Na_2CO_3]^0 = n[CO_3^{2-}]^0 = n[HCO_3^-] + n[CO_3^{2-}] \quad \text{Equation 7}$$

The starting number of moles of disodiumcarbonate, $n[Na_2CO_3]^0$, for obtaining a pH of 9.0 is then equal to $$1.05 \times n(ASA)^0 = 1.05 \times 0.00167 = 1.18 \cdot 10^{-3} \text{ mol} \quad \text{Equation 8}$$

Example 5 Test of a Two-Component System Comprising ASA Together with a Salt of Carbonic Acid in One Component In the following example ASA and the disodium salt of carbonic acid ($Na_2CO_3$) are dissolved at the same time in 15 ml pure water.

300 mg ASA and 258-263 mg sodium carbonate ($Na_2CO_3$) were placed together in the powder compartment of the test device used in example 1, and 15 ml of pure water was filled into the container (bottle) of said device. After releasing the ASA and sodium carbonate into the water, the solution was shaken until all ASA was dissolved.

It took approx. 120 sec. before ASA was dissolved. The pH of the solutions after dissolution of ASA and the carbonate salt was between 9.41-9.43.

The invention claimed is:

1. A two-component system comprising
a first and a second component which are physically separated,
wherein the first component comprises a therapeutically effective amount of acetylsalicylic acid (ASA) and optionally one or more pharmaceutically acceptable excipients;
wherein the second component comprises an aqueous solution comprising at least one pharmaceutically acceptable salt of carbonic acid and optionally one or more pharmaceutically acceptable excipients; provided that the second component does not comprise a salt of citric acid; and
wherein an aqueous solution of ASA with a pH above approximately 7.5 is obtained upon mixing of the first and second components,
or
wherein the first component comprises a therapeutically effective amount of acetylsalicylic acid (ASA) and optionally one or more pharmaceutically acceptable excipients; and
wherein the second component comprises an aqueous solution comprising at least one pharmaceutically acceptable salt of carbonic acid and optionally one or more pharmaceutically acceptable excipients;
wherein at least one pharmaceutically acceptable salt of an acid selected from the group consisting of sorbic acid and/or benzoic acid is comprised in the first component together with ASA, in the second component together with the salt of carbonic acid, or in both the first and the second component; and
wherein an aqueous solution of ASA with a pH above approximately 7.5 is obtained upon mixing of the first and second components.

2. The two-component system according to claim 1, wherein the salt of carbonic acid is selected from the group consisting of sodium carbonate and potassium carbonate.

3. The two-component system according to claim 1, wherein the salt of sorbic acid is potassium sorbate and the salt of benzoic acid is sodium benzoate.

4. The two-component system according to claim 1, wherein the volume of the aqueous solution of the second component is in the range of 6 ml-50 ml.

5. The two-component system according to claim 1, wherein the amount of acetylsalicylic acid in the first component is in the range of 300 to 325 mg, and the volume of the second component is in the range of 8 to 15 ml.

6. A container comprising a first and a second chamber, wherein the first chamber comprises a therapeutically acceptable amount of acetylsalicylic acid (ASA) and optionally one or more pharmaceutically acceptable excipients; and wherein the second chamber comprises an aqueous solution comprising at least one pharmaceutically acceptable salt of carbonic acid and optionally one or more pharmaceutically acceptable excipients; provided that the second chamber does not comprise a salt of citric acid; and wherein an aqueous solution of ASA with a pH above approximately 7.5 is obtained upon mixing of the content of the two chambers, or wherein the first chamber comprises a therapeutically acceptable amount of acetylsalicylic acid (ASA) and optionally one or more pharmaceutically acceptable excipients; and wherein the second chamber comprises an aqueous solution comprising at least one pharmaceutically acceptable salt of carbonic acid and optionally one or more pharmaceutically acceptable excipients; and wherein at least one pharmaceutically acceptable salt of an acid selected from the group consisting of sorbic acid and/or benzoic acid is comprised in the first chamber together with ASA, in the second chamber together with the salt of carbonic acid, or in both the first and the second chamber; and wherein an aqueous solution of ASA with a pH above approximately 7.5 is obtained upon mixing of the content of the two chambers.

7. A container according to claim 6, wherein the salt of carbonic acid is selected from the group consisting of sodium carbonate and potassium carbonate.

8. A container according to claim 6, wherein the salt of sorbic acid is potassium sorbate and the salt of benzoic acid is sodium benzoate.

9. A method for treating imminent myocardial infarct in a person in need thereof by administering an aqueous solution of acetylsalicylic acid comprising the steps of:
a) providing the two-component system according to claim 1;
b) mixing the first component of said system with the aqueous solution of the second component, and thereby obtaining an aqueous solution of acetylsalicylic acid;
c) administering to the person in need thereof the mixture obtained in step b).

10. The method according to claim 9, wherein the aqueous solution of acetylsalicylic acid is obtained within approximately one minute or less.

11. A method for treating imminent myocardial infarct in a person in need thereof by administering an aqueous solution of acetylsalicylic acid comprising the steps of:
   a. providing the container according to claim 6;
   b. mixing the content of the first chamber of said container with the aqueous solution of the second chamber, and thereby obtaining an aqueous solution of acetylsalicylic acid;
   c. administering to the person in need thereof the mixture obtained in step b).

12. The method according to claim 11, wherein the aqueous solution of acetylsalicylic acid is obtained within approximately one minute or less.

\* \* \* \* \*